(12) United States Patent
Gliner et al.

(10) Patent No.: US 7,945,330 B2
(45) Date of Patent: May 17, 2011

(54) SYSTEMS AND METHODS FOR AUTOMATICALLY OPTIMIZING STIMULUS PARAMETERS AND ELECTRODE CONFIGURATIONS FOR NEURO-STIMULATORS

(75) Inventors: Bradford Evan Gliner, Sammamish, WA (US); Jeffrey Balzer, Allison Park, PA (US); Andrew D. Firlik, New Canaan, CT (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 229 days.

(21) Appl. No.: 12/244,610

(22) Filed: Oct. 2, 2008

(65) Prior Publication Data

US 2009/0093862 A1   Apr. 9, 2009

Related U.S. Application Data

(60) Division of application No. 11/407,684, filed on Apr. 20, 2006, now abandoned, which is a continuation of application No. 09/978,134, filed on Oct. 15, 2001, now Pat. No. 7,305,268, which is a continuation-in-part of application No. 09/802,808, filed on Mar. 8, 2001, now Pat. No. 7,010,351.

(60) Provisional application No. 60/217,981, filed on Jul. 13, 2000.

(51) Int. Cl.
*A61N 1/36* (2006.01)

(52) U.S. Cl. .......................................... 607/45; 607/46

(58) Field of Classification Search .................... 607/45, 607/46
See application file for complete search history.

(56) References Cited

U.S. PATENT DOCUMENTS

| 5,925,070 | A | * | 7/1999 | King et al. | ...................... 607/46 |
| 6,463,328 | B1 | * | 10/2002 | John | ............................... 607/45 |
| 6,735,475 | B1 | * | 5/2004 | Whitehurst et al. | ........... 607/46 |
| 2002/0042563 | A1 | * | 4/2002 | Becerra et al. | ................ 600/407 |

* cited by examiner

*Primary Examiner* — Scott M Getzow
*Assistant Examiner* — Joseph M Dietrich
(74) *Attorney, Agent, or Firm* — Melissa Acosta; Christopher S. L. Crawford; Craig Hoersten

(57) ABSTRACT

Methods and devices for automatically optimizing the stimulus parameters and/or the configuration of electrodes to provide neural stimulation to a patient. In one embodiment, a system includes an electrode array having an implantable support member configured to be implanted into a patient and a plurality of therapy electrodes carried by the support member. The system can also have a pulse system operatively coupled to the therapy electrodes to deliver a stimulus to the therapy electrodes, and a sensing device configured to be attached to a sensing location of the patient. The sensing device generates response signals in response to the stimulus. The system can also include a controller operatively, coupled to the pulse system and to the sensing device. The controller includes a computer operable medium that generates command signals that define the stimulus delivered by the pulse system, evaluates the response signals from the sensing device, and determines a desired configuration for the therapy electrodes and/or a desired stimulus to be delivered to the therapy electrodes.

6 Claims, 12 Drawing Sheets

○ INACTIVE ELECTRODE
● ACTIVE ELECTRODE (+ OR −)

○ INACTIVE ELECTRODE
● ACTIVE ELECTRODE (+ OR −)

○ INACTIVE ELECTRODE
● ACTIVE ELECTRODE (+ OR −)

○ INACTIVE ELECTRODE
● ACTIVE ELECTRODE (+ OR −)

SYSTEMS AND METHODS FOR AUTOMATICALLY OPTIMIZING STIMULUS PARAMETERS AND ELECTRODE CONFIGURATIONS FOR NEURO-STIMULATORS

CROSS-REFERENCE TO RELATED APPLICATION(S)

This application is a divisional of U.S. application Ser. No. 11/407,684, filed Apr. 20, 2006, now abandoned which is a continuation of U.S. application Ser. No. 09/978,134, filed Oct. 15, 2001, which issued on Dec. 4, 2007 as U.S. Pat. No. 7,305,268, which is a continuation in part of U.S. application Ser. No. 09/802,808 filed Mar. 8, 2001, now U.S. Pat. No. 7,010,351, issued Mar. 7, 2006, which claims priority to U.S. Application No. 60/217,981 filed Jul. 13, 2000, all of which are incorporated herein by reference in their entireties.

TECHNICAL FIELD

The present disclosure is related to systems and methods for automatically optimizing the configuration of therapy electrodes and/or the stimulus parameters of the electrical or magnetic waveforms applied to a target stimulation site of a patient.

BACKGROUND

A wide variety of mental and physical processes are known to be controlled or influenced by neural activity in the central and peripheral nervous systems. For example, the neural-functions in some areas of the brain (i.e., the sensory or motor cortices) are organized according to physical or cognitive functions. There are also several other areas of the brain that appear to have distinct functions in most individuals. In the majority of people, for example, the areas of the occipital lobes relate to vision, the regions of the left interior frontal lobes relate to language, and the regions of the cerebral cortex appear to be consistently involved with conscious awareness, memory and intellect. The spinal cord is also organized so that specific regions of spinal cord are related to particular functions. Because of the location-specific functional organization of the central nervous system in which neurons at discreet locations are statistically likely to control particular mental or physical functions in normal individuals, stimulating neurons at selected locations of the central nervous system can be used to effectuate cognitive and/or motor functions throughout the body.

The neural activity in the central nervous system can be influenced by electrical and/or magnetic energy that is supplied from an external source outside of the body. Various neural functions can thus be promoted or disrupted by applying an electrical current to the cortex or other part of the central nervous system. As a result, the quest for treating or augmenting neural functions in the brain, spinal cord, or other parts of the body have led to research directed toward using electricity or magnetism to control these functions.

In several existing applications, the electrical or magnetic stimulation is provided by a neural-stimulator that has a plurality of therapy electrodes and a pulse system coupled to the therapy electrodes. The therapy electrodes can be implanted into the patient at a target site for stimulating the desired neurons. For example, one existing technique for masking pain in the lower extremities of a patient is to apply an electrical stimulus to a desired target stimulation site of the spinal cord. Although determining the general location of the target stimulation site may be relatively straight forward, identifying the specific configuration of electrodes for applying the stimulus will generally vary for specific patients.

The conventional procedure for optimizing the configuration of therapy electrodes involves several steps and relies on the subjective input from the patient. Conventional techniques generally involve rendering the patient unconscious, implanting an electrode array in the patient at the stimulation site, and then letting the patient regain consciousness. After the patient is conscious, the particular configuration of electrodes is optimized for that patient by selecting different combinations of the therapy electrodes and applying a constant electrical stimulus. The patient subjectively evaluates the effectiveness of each stimulus by indicating the degree to which the stimulus masks the pain. After testing the various configurations of therapy electrodes and deciding upon a desired electrode configuration according to the input of the patient, the patient is rendered unconscious for a second time to close the electrode array in the patient.

A similar procedure can be followed for determining the desired configuration of therapy electrodes for intra-cranial electrical stimulation. For example, a device for stimulating a region of the brain is disclosed by King in U.S. Pat. No. 5,713,922. King discloses a device for cortical surface stimulation having electrodes mounted on a paddle. The paddle can be implanted under the skull of the patient so that the electrodes are on the surface of the brain in a fixed position. King also discloses that the electrical pulses are generated by a pulse generator implanted in the patient remotely from the cranium (e.g., subclavicular implantation). The pulse generator is coupled to the electrodes by a cable that extends from the paddle, around the skull, and down the neck to the sub-clavicular location of the pulse generator.

King discloses implanting the electrodes in contact with the surface of the cortex to create paresthesia, which is a vibrating or buzzing sensation. More specifically, King discloses inducing paresthesia in large areas by placing the electrodes against particular regions of the brain and applying an electrical stimulus to the electrodes. This is similar to implanting therapy electrodes at the spinal cord of a patient for masking pain in the lower extremities of a patient, and thus King appears to require stimulation that exceeds the membrane activation threshold for a population of neurons at the electrodes (supra-threshold stimulation). King further discloses applying a stimulus to one set of electrodes, and then applying a stimulus to a separate configuration of electrodes to shift the location of the paresthesia.

One problem of the procedures for optimizing the configuration of therapy electrodes for either spinal or cortical stimulation is that existing systems and methods are expensive and time consuming. First, it is expensive to render the patient unconscious, implant the neural-stimulators in the patient, then wait for the patient to regain consciousness, then test various electrode configurations by asking the patient to subjectively estimate the degree to which the particular stimulus masks the pain, and then finally render the patient unconscious again to complete the implantation. Second, it can be a reasonably high risk operation because the patient is placed under general anesthesia at two separate stages of the process. It will be appreciated that this is an extremely long process that requires highly skilled doctors and personnel to attend to the patient for a significant period of time. Moreover, the patient occupies costly operating rooms and utilizes expensive equipment throughout the process. Third, relying on the subjective response from the patient may not provide accurate data for evaluating minor variances in the results. Fourth, the patient may experience pain or discomfort because some configurations may provide high intensity stimulation that exceeds the sensory level of stimulation. Therefore, existing systems for determining a desired configuration of electrodes to apply a neural-stimulus to specific patients are expensive, time consuming, potentially painful, and may not determine the most effective electrode configuration.

Another drawback of configuring the therapy electrodes using existing systems and methods is that the procedures are not effective for on-going use. This is because the patient's condition changes continually. For example, the location of the pain or the sensation typically shifts over time such that the optimal configuration of the electrodes at one point of the therapy may not mask the pain after a period of time. A large number of patients accordingly terminate electrical therapies for paresthesia within one year because of such a shift in the location of the pain/sensation. Therefore, although electrical stimulation for masking pain, inducing or enhancing plasticity, and other reasons appears to be very promising, it has not yet gained wide acceptance because of the drawbacks of configuring the therapy electrodes to apply an effective stimulus to different patients over a long period of time.

Additionally, it is also difficult to optimize the parameters of the electrical or magnetic stimulus. For example, even when a desired configuration of therapy electrodes is used, different waveforms can produce different results in each patient. Determining the stimulus parameters of the waveform can be even more time consuming than determining the desirable configuration of therapy electrodes because it involves testing a large number of independent variables. In a biphasic pulse train, for example, the stimulus parameters can include (a) the intensity of the electrical current, (b) the time of the stimulus of the first phase, (c) the time of the stimulus of the second phase, (d) the total time of the stimulus pulse, (e) the frequency of the stimulus pulse, (f) the pulse duty cycle, (g) the burst time of the stimulus, (h) the burst repetition rate of the stimulus, and (i) additional variables. Because of the large number of stimulus parameters, a particular waveform for the stimulus is typically selected for a given treatment for all patients such that the parameters for stimulus itself are not optimized.

In light of the several drawbacks for existing techniques of applying electrical or magnetic neural-stimulation to produce desired results, there is a significant need to enhance the procedures for applying such stimulus to individual patients. For example, it would be desirable to have more cost effective and less time consuming procedures for determining an effective configuration of therapy electrodes and stimulus parameters. Additionally, it would be desirable to update the electrode configuration and stimulus parameters in each individual patient without surgically operating on the patient to compensate for shifts in the target stimulation site.

DETAILED DESCRIPTION

The following disclosure describes several methods and apparatus for automatically determining the configuration of therapy electrodes and/or the parameters for the stimulus to treat or otherwise effectuate a change in neural-functions of a patient. Several embodiments of methods in accordance with the invention are practiced using a computer to automatically implement such processes, but it is not necessary to use a computer in all of the embodiments. The specific details of certain embodiments of the invention are set forth in the following description and in FIGS. 1-7 to provide a thorough understanding of these embodiments to a person of ordinary skill in the art. More specifically, several embodiments of a system in accordance with the invention are described with reference to FIG. 1, and then several embodiments of methods for determining a desired configuration of therapy electrodes and/or stimulus parameters are described with reference to FIGS. 2-7. A person skilled in the art will understand that the present invention may have additional embodiments, or that the invention can be practiced without several of the details described below.

Figure 1:
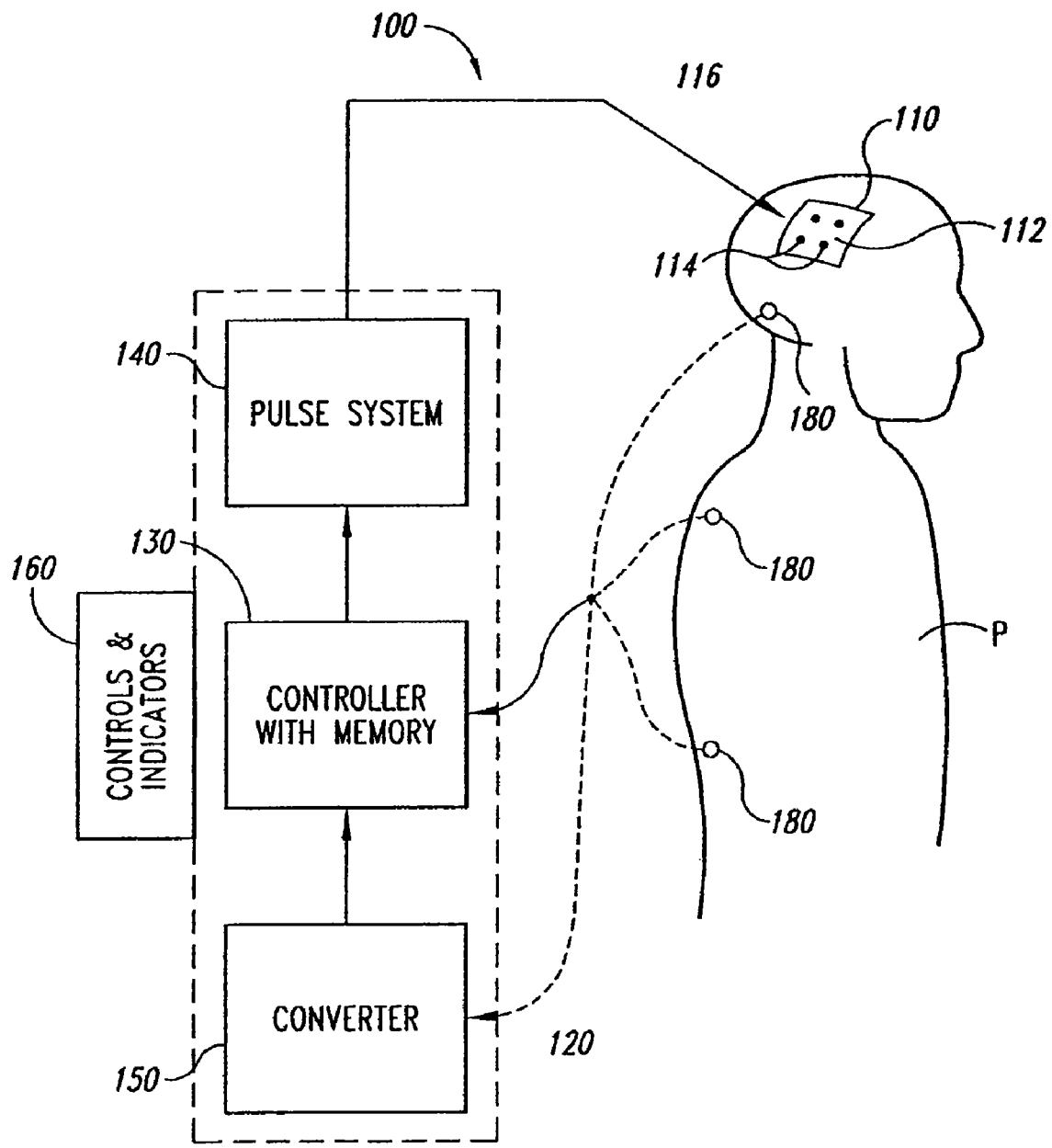
FIG. 1 is a schematic illustration of a system for automatically optimizing the configuration of the electrodes and/or the stimulus parameters in accordance with an embodiment of the invention.

A. Systems for Automatically Optimizing Therapy Electrode Configurations and/or Stimulus Parameters FIG. 1 illustrates an embodiment of a system for providing neuro-stimulation to a patient that can automatically optimize (a) the configuration of therapy electrodes, (b) the waveform parameters for the electrical stimulus, and/or (c) additional stimulation parameters. In this embodiment, the system 100 comprises an electrode array 110, a stimulus unit 120 operatively coupled to the electrode array 110, and at least one sensing device 180 operatively coupled to the stimulus unit 120. The electrode array 110 and the sensing unit 180 can be operatively coupled to the stimulus unit 120 by a direct connection (e.g., wires, cables, or fiber optical lines) or an indirect connection (e.g., RF energy, magnetic energy, infrared, etc.).

The electrode array 110 can include a support member 112 and a plurality of electrodes 114 that are carried by the support member 112. The electrode array 110 is generally configured to be implanted into a patient P for cortical stimulation, deep brain stimulation, spinal cord stimulation, cardiac stimulation, or stimulation of other parts of the body. For example, the electrode array 110 can be a cortical neural-stimulation device, such as one of the devices described in U.S. application Ser. No. 09/802,808 incorporated by reference above. The electrode array 110 can alternatively be a grid having a plurality of discrete electrodes 114 arranged in an X-Y coordinate system or another type of coordinate system. The therapy electrodes 114 can be independently coupled to the stimulus unit 120 by a link 116. In one embodiment, the link 116 is a wire or another type of conductive line, but in alternate embodiments the link 116 can be an indirect link (e.g., infrared, magnetic or RF energy). The link 116 can accordingly be a direct connection or an indirect connection to operatively couple the therapy electrodes 114 to the stimulus unit 120. It will be appreciated that many of the electrode arrays can be implanted at the spinal cord for spinal cord stimulation.

The stimulus unit 120 can include a controller 130 with a processor, a memory, and a programmable computer medium. The controller 130, for example, can be a computer and the programmable computer medium can be software loaded into the memory of the computer and/or hardware that performs the processes described below. The stimulus unit 120 can further include a pulse system 140, a converter 150, and a plurality of controls/indicators 160. The pulse system 140 can generate and send energy pulses to the electrode array, and the converter 150 can receive signals from the sensing device 180. The pulse system 140 and the converter 150 are both operatively coupled to the controller 130. The controls and indicators 160 can include a computer display, an input/output device (e.g., a keyboard, touch sensitive screen, etc.), or other types of devices commonly used to enter commands or receive output from computers.

The electrode array 110 and the pulse system 140 can be integrated into a single stimulation apparatus that can be implanted into the patient, as described in U.S. application Ser. No. 09/082,808. One example of an integrated pulse system 140 and electrode array 110 is configured to be implanted into the skull of the patient so that the electrodes contact the pia matter of the cortex. Such a device can have an internal power source that can be implanted into the patient and/or an external power source coupled to the pulse system via electromagnetic coupling or a direct connection. In alternate embodiments, the pulse system 140 is an external unit that is not implanted into the patient. The external pulse unit 140 can provide the electrical stimulus to the therapy electrodes 114 using RF energy, electromagnetism, or wire terminals exposed on the scalp of the patient P.

The sensing device 180 can be an electrode that produces an analog signal, and the converter 150 can convert the analog signal to a digital signal for processing by the controller 130. The sensing device 180 can be an implantable electrode that can be implanted at a number of different locations according to the desired response of the stimulus applied to the therapy electrodes 114. In alternate embodiments, the sensing device 180 can be an imaging device (e.g., an fMRI apparatus), an ultrasound apparatus, an EEG, a device that detects somatosensory evoked potentials, or another suitable apparatus for determining a response in the patient P to a stimulus applied to the therapy electrodes 114. The sensing device can alternatively detect behavioral responses. In an alternate embodiment, the sensing device 180 can produce a digital output and be coupled directly to the controller 130. Therefore, the converter 150 may only be used in some of the embodiments of the system 100.

The system 100 can automatically test the efficacy of various electrode configurations and stimulus parameters either with or without subjective input from the patient. In operation, the controller 130 sends command signals to the pulse system 140 defining the configuration of active electrodes and the waveform parameters for the stimulus. The pulse system 140 generates and sends a single pulse or pulse train to the active therapy electrodes in accordance with the command signals, and the sensing device 180 senses the neural responses, motor responses, or other types of responses to the stimulus. The sensing device 180 also sends signals corresponding to the magnitude of the responses to the controller 130, which compares the responses to previous responses and/or empirical responses for the type of therapy stored in the memory of the controller. The controller 130 then adjusts the configuration of active therapy electrodes and/or the waveform parameters of the stimulus to optimize the therapy for the particular patient. Several methods for using embodiments of the system 100 for supra- and sub-threshold neural-stimulation therapies are described below.

Figure 2:
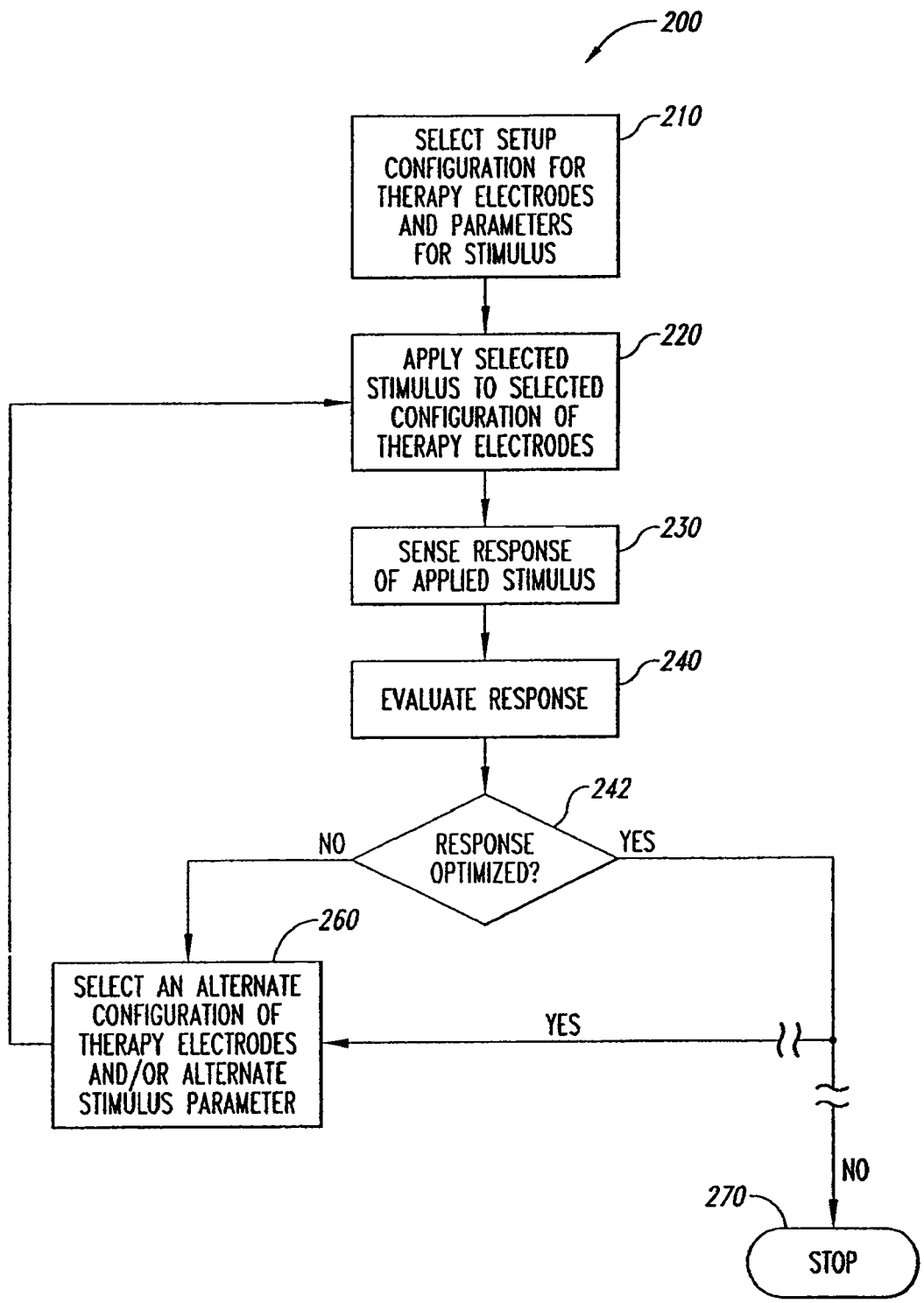
FIG. 2 is a flow diagram illustrating a method for automatically optimizing the configuration of electrodes and/or the stimulus parameters in accordance with one embodiment of the invention.

B. Methods of Optimizing Electrode Configurations and Stimulus Parameters for Neuro-Stimulation FIGS. 2-7 illustrate several embodiments of methods in accordance with the invention that can be practiced using the stimulator system 100 described above. FIG. 2, for example, is a flow diagram illustrating an optimization process 200 that can be executed, at least in part, in a computer for automatically optimizing the configuration of therapy electrodes and/or the waveform parameters for the stimulus. The optimization process 200 generally starts after the therapy electrode array has been installed at a target stimulation site using surgical techniques known in the art and a sensing device has been positioned to sense a response to the electrical stimulus applied to the therapy electrodes.

After the therapy electrode array has been installed and the sensing device is ready to sense a response in the patient, the optimization process 200 begins with a setup procedure 210 in which a setup configuration of therapy electrodes and the waveform parameters for a control stimulus are selected. The controller can select the setup configuration for the electrodes and the control stimulus by retrieving predetermined setup values stored in a setup database in the memory of the controller. The setup database can contain at least one setup configuration for the therapy electrodes and at least one set of waveform parameters for the control stimulus. In several embodiments, a plurality of different setup configurations for the electrodes and the stimulus parameters can be stored in a database so that the system 100 can be used for many different types of neural therapies and procedures. An alternate embodiment can involve manually inputting the setup configuration for the electrodes and the waveform parameters for the control stimulus either in lieu of or in addition to having the controller retrieve setup data from memory. A practitioner, for example, can select the setup data from pull-down menus provided by the system 100 or manually key in the data.

The setup configurations for the therapy electrodes and the waveform parameters for control stimuli can be determined by manually performing optimization procedures on test groups of patients for each type of therapy. The optimal setups can be correlated with the particular therapy (e.g., enhancing neural plasticity in the cortex, masking pain, etc.), the particular target site, and the patient factors. For example, a first electrode configuration and control stimulus can be determined for sub-threshold cortical neural stimulation to restore functionality of a limb that was affected by a stroke or other type of brain damage; a second electrode configuration and control stimulus can be determined for cortical neural stimulation to enhance learning capabilities; a third electrode configuration and control stimulus can be determined for spinal stimulation to mask pain; and a fourth electrode configuration and control stimulus can be determined for sub- or supra-threshold stimulation applied to the cortex. It will be appreciated that many additional electrode configurations and stimulus parameters can be determined for other types of therapies such that the foregoing is not exhaustive of the various types of setup configurations.

Referring again to FIG. 2, the optimization process 200 continues with a stimulating procedure 220 and then a sensing procedure 230. The stimulating procedure 220 involves applying an electrical stimulus to a configuration of the therapy electrodes. Several iterations of the stimulation procedure 220 are generally performed several times at different stages throughout the optimization process 200, and the configuration of the electrodes and/or the stimulus parameters can be changed at each iteration of the stimulation procedure 220. For example, the initial iteration of the stimulating procedure 220 can involve applying the control stimulus to the setup configuration of therapy electrodes. Subsequent iterations of the stimulation procedure 220 can involve applying (a) the control stimulus to an alternate configuration of therapy electrodes; (b) an alternate stimulus with a different waveform to the setup electrode configuration; and/or (c) alternate stimuli with different waveforms to alternate electrode configurations. As explained above with reference to FIG. 1, the controller carries out the stimulation procedure 220 by sending command signals to the pulse system, which in turn generates and transmits energy having the parameters for the stimulus to the selected configuration of active therapy electrodes.

The sensing procedure 230 is generally performed after each iteration of the stimulation procedure 220. The sensing procedure 230 involves monitoring a location in the patient for a response to the stimulus applied in the stimulation procedure 220. The location for sensing the response and the particular type of response that is measured varies according to the particular type of therapy and other factors. In general, the physiologic outcome that the response measures can be categorized into three general areas: (1) cortical; (2) peripheral; and (3) functional. The types of measurements for monitoring cortical physiologic outcomes include: (a) action potential generation of the neurons; (b) excitability changes of the neurons measured waveform characteristics of EEG or field potentials within the cortex; (c) blood flow (e.g., doppler measurements); (d) thermal changes; (e) pulse oxymetry; (f) chemical metabolites; and (g) imaging techniques (e.g., functional MRI, MR spectroscopy, diffusion MRI, PET, CT, etc.). The types of measurements for monitoring peripheral physiologic outcomes include: (a) EMG (surface, percutaneous, or implanted); (b) external potentiometer or other forms of physiologic input; and (c) motion detectors (e.g., accelerometers). The types of measurements for monitoring functional physiologic outcomes include: (a) force/strength tests; (b) dexterity tests; (c) speed/reflex tests; and (d) performing complex tasks.

Several types of measurements that monitor the physiologic outcomes can be automated so that they generate signals which can be processed by the controller either with or without subjective input from the patient. In the case of EMG measurements for sensing peripheral responses to the applied stimulus, the electrical signals from the EMG sensors are automatically received and processed by the controller. In other applications, the data sensed by functional MRI, blood flow monitors, thermal monitors, pulse oxymeters, PET, MR spectroscopy, accelerometers, etc. can be digitized and process by the controller in a similar manner. In this manner, the stimulating procedure 220 and the sensing procedure 230 can be automated using a controller with the appropriate hardware and/or software.

The optimization process 200 also includes performing an evaluation procedure 240 after one or more iterations of the stimulating procedure 220 and the sensing procedure 230. The evaluation procedure 240 can involve a determination routine 242 in which a sensed response from the sensing procedure 230 is compared with a desired response range and/or other responses from previous iterations of the stimulation procedure 220 and the sensing procedure 230. Based upon whether the sensed response is within a desired range and/or shows an improvement compared to previous responses or target ranges, the controller can automatically test the effectiveness of other electrode configurations and stimulus parameters. For example, if the response is not within the desired response range, then the determination routine 242 directs the controller to select an alternate configuration for the therapy electrodes and/or alternate parameter for the stimulus. Alternatively, in one embodiment when the sensed response is within the desired response range, the determination routine 242 can direct the controller to proceed directly to a stop 270 and indicate that the configuration of therapy electrodes and the parameters for the stimulus have been optimized to treat the specific patient. In another embodiment when the sensed response is within the desired response range, the determination routine 242 directs the controller to select additional alternate configurations of the therapy electrodes and/or stimulus parameters to discover whether a more effective response can be achieved.

The process of selecting alternate therapy electrode configurations or stimulus parameters is performed by an analyzing procedure 260. In one embodiment, the analyzing procedure 260 is predicated upon the understanding that the electrode configuration and each of the stimulus parameters are independent variables that can be individually optimized while keeping the other variables constant. The analyzing procedure 260, therefore, can proceed by keeping one of the configuration of the therapy electrodes or the stimulus parameters constant and then progressively adjusting the other of these variables until the most effective result is obtained for the adjusted variable. For example, when the analyzing procedure 260 selects alternate stimulus parameters, it typically maintains the previous configuration of therapy electrodes and it adjusts only one of the stimulus parameters at a time. Conversely, the analyzing procedure 260 can keep the same stimulus parameters and select alternate configurations of therapy electrodes. The analyzing procedure 260 can select alternate inputs for the stimulus parameters and/or the electrode configurations by dynamically estimating new parameters based on projected response patterns for using empirical data developed for particular therapies and/or actual responses from previous stimuli applied to the patient. In one embodiment, the controller automatically analyzes the responses from previous stimulating procedures 220 to determine a pattern of improved or degraded effectiveness of the corresponding configurations of therapy electrodes and stimulus parameters that were applied in the iterations of the stimulation procedure 220. Based upon the pattern of responses, the analyzing routine 260 can then incrementally change one of the variables in a manner that concurs with a pattern showing improved responses or moves away from the pattern that shows deteriorated responses.

A basic example of the analyzing routine 260 involves optimizing the frequency of the electrical stimulus. As such, the configuration of electrodes and the other stimulus parameters remain constant for several iterations of the applying procedure 220. In one iteration a stimulus having a first frequency (e.g., 50 Hz) may produce marginal results as determined by the sensing and evaluation procedures 230 and 240. Without additional data, the analyzing procedure 260 selects a second stimulus with a second frequency either less or greater than the first frequency to get a general understanding of whether higher or lower frequencies produce more efficacious results. The controller, for example, can select a second frequency of 25 Hz. If a frequency of 25 Hz produces better results than 50 Hz, the controller can select still lower frequencies in the analyzing procedure 260; but, assuming for the sake of this example that a frequency of 25 Hz produces a worse result than 50 Hz, then the controller can select a third frequency higher than the second frequency (e.g., 100 Hz). If the higher third frequency (e.g., 100 Hz) produces a better result than the first frequency (e.g., 50 Hz), then the controller can select a still higher fourth frequency (e.g., 200 Hz) in a subsequent iteration of the procedure. The method 200 can continue in this manner by adjusting variables in a direction that produces better results until the results begin to deteriorate. At this point, it is expected that the optimal value for the variable is bracketed between the last value selected for the variable and the value of the iteration immediately preceding the penultimate iteration (i.e., the second-to-the-last iteration).

Several embodiments of the optimization procedure 200 that use the system 100 are expected to reduce the cost and time for optimizing the configuration of the therapy electrodes and the stimulus parameters. One feature of the optimizing method 200 is that the pulse system and the therapy electrodes can be an integrated unit that is implanted into the patient and controlled externally from the patient such that an external controller can adjust the variables (e.g., electrode configuration and/or stimulus parameters) without requiring opening the patient for access to the pulse system and/or the therapy electrodes. One benefit of this feature is that several different electrode configurations and stimulus parameters can be adjusted after implanting the electrode array, and the variables can also be tested rather quickly because the controller can automatically adjust the variables and apply the stimulus to the therapy electrodes in a manner that is expected to be much faster than manually adjusting the variables. Another benefit of this feature is that the patient need only be subject to a single application of an anesthetic because the patient can be closed up soon after implanting the electrode array and the test can be performed after closing the patient. As a result, several embodiments of the optimization procedure 200 are expected to reduce the time and costs for determining a desirable electrode configuration and stimulus parameters.

Several embodiments of the optimization procedure 200 are also expected to provide better results than relying solely on the subjective input of the patient. Another aspect of several embodiments of the system 100 is that the sensing device provides objective criteria that measures the response to the stimuli. This feature is expected to provide better accuracy in determining the effectiveness of the individual stimuli applied to the therapy electrodes. Moreover, the optimization procedure 200 can also expediently optimize the waveform parameters in addition to optimizing the configuration of therapy electrodes such that both the electrical components of the stimulus and the location(s) where the stimulus is applied are optimized for specific patients.

Another feature of several embodiments of the optimization method 200 using the system 100 is that they are expected to provide more effective therapies over a long period of time without additional surgical procedures. One feature that provides this benefit is that the pulse system and the electrode array can be implanted into the patient and controlled externally from the patient. As a result, when the effectiveness of the therapy degrades because the target site shifts or another variable changes, the sensing device 180 can be positioned relative to the patient and coupled to the controller to re-optimize the electrode configuration and/or the stimulus parameters without having to perform surgery on the patient. The system 100 can accordingly be operated using embodiments of the optimization procedure 200 at any time to compensate for shifts in the target location. Several embodiments of the optimization procedure 200 that use the system 100 are accordingly expected to provide more effective therapies for ongoing applications.

Still another benefit of several embodiments of the method 200 is that they are expected to be more comfortable for patients. One feature of the method 200 is that the sensing procedure can sense responses at levels that the patient cannot feel any sensations. As a result, is it not likely that the application of the stimulus will cause pain or discomfort.

Figure 3:
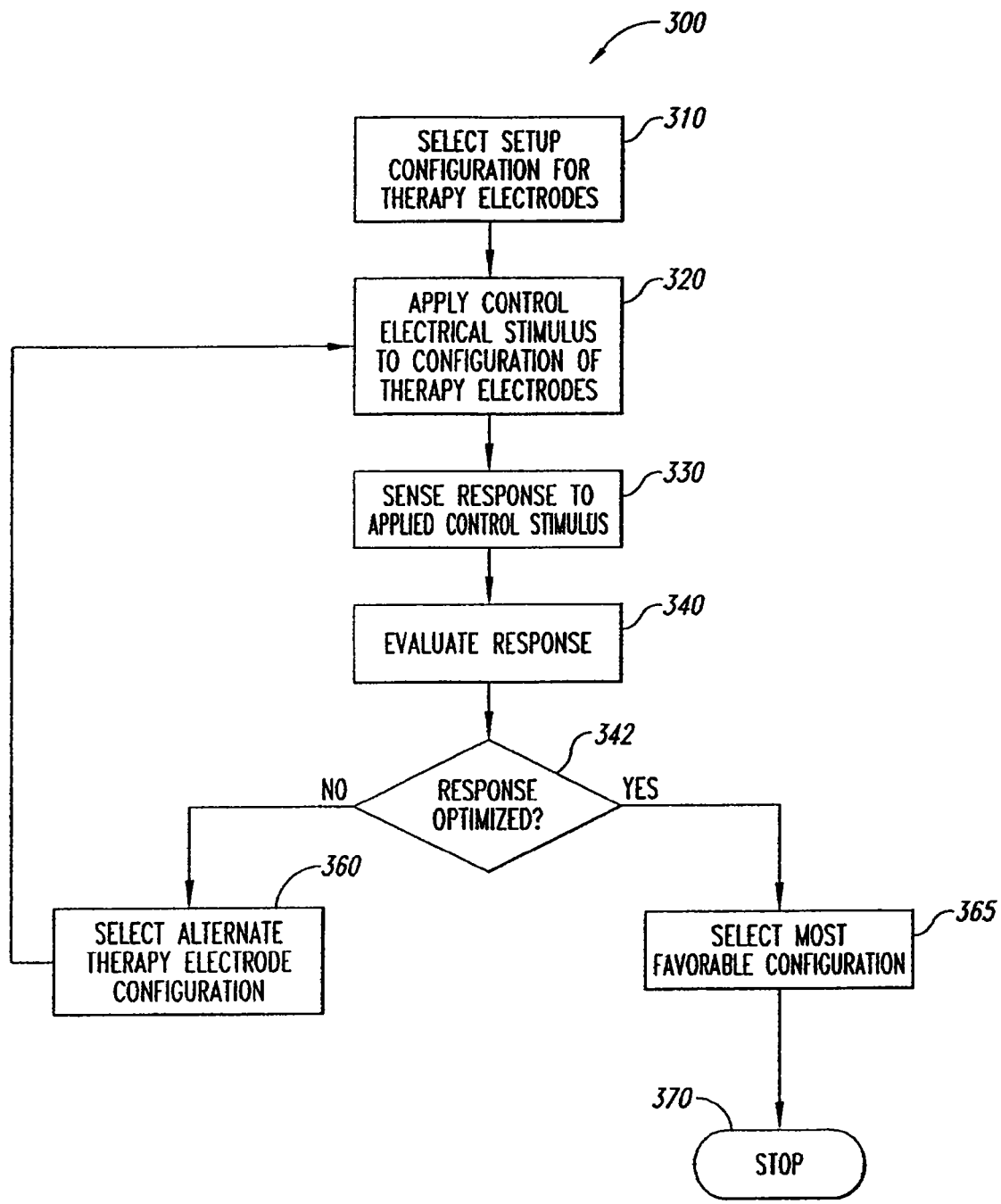
FIG. 3 is a flow diagram of an embodiment of a method for optimizing the configuration of therapy electrodes that can be used in the method of FIG. 2 in accordance with an embodiment of the invention.

FIG. 3 is a flow diagram illustrating one embodiment of a method for optimizing the configuration of therapy electrodes in accordance with the invention. In this embodiment, the method 300 can include a setup procedure 310 in which a setup configuration of therapy electrodes is selected. The setup configuration of therapy electrodes can be based upon historical data obtained from previous optimization procedures for specific patients or different types of therapies. After performing the setup procedure 310, the method 300 continues with a stimulating procedure 320 in which a control electrical stimulus is applied to the selected configuration of therapy electrodes. A response in the patient to the applied control stimulus is then sensed in a sensing procedure 330, which is generally performed after each iteration of the stimulating procedure 320. The stimulating procedure 320 and the sensing procedure 330 can be similar to those described above with reference to FIG. 2, except that the stimulating procedure 320 involves applying the same control stimulus for each iteration. The primary difference, therefore, is that the configuration of therapy electrodes can be changed for each iteration of the stimulating procedure 320.

The method 300 continues with an evaluation procedure 340 in which the sensed response from the sensing procedure 330 is compared with a predetermined range of desired responses and/or previous responses from the sensing procedure 330. The evaluation procedure 340 can have several different embodiments. The evaluation procedure 340, for example, can include a determination routine 342 that determines whether the sensed response is the optimized response. In one embodiment, the sense response is considered to be optimized when it is within a desired range of responses. The method 300 can accordingly proceed to stop when such a response is sensed. In another embodiment, the sensed response is considered to be optimized when it provides the best result of all possible configurations of electrodes. This embodiment generally involves applying the control stimulus to all possible configurations of electrodes before identifying the optimized electrode configuration. In still another embodiment, the sensed response is the optimized response when it provides the most effective result compared to other responses without testing all of the possible configurations of electrodes. This embodiment involves testing a number of electrode configurations, identifying a trend in electrode configurations that produce effective results, and determining if or when the trend no longer holds true. It will be appreciated that the evaluation procedure 340 can have several additional or different embodiments.

The method 300 can continue with an analyzing procedure 360 that selects an alternate therapy electrode configuration. The alternate therapy electrode configuration selected in the analyzing procedure 360 can be determined by comparing previous responses to other configurations of therapy electrodes to develop a pattern of improved responses and selecting a configuration that is expected to continue the trend. Alternatively, the analyzing procedure 360 can simply select another therapy electrode configuration that has not yet been tested. The method can also include a final selection procedure 365 that selects the optimized configuration of the therapy electrodes based upon the sensed responses. The process 300 can then terminate with a final stop procedure 370 in which the optimized electrode configuration is stored in memory, displayed to a practitioner, or otherwise presented for use.

FIGS. 4A-4L illustrate several examples of therapy electrode configurations that can be selected in the analyzing procedure 360 and then tested in the stimulating procedure 320, the sensing procedure 330, and the evaluation procedure 340. In these embodiments, a therapy electrode array 400 for use with the system 100 (FIG. 1) can include an implantable support member 410 and a plurality of electrodes 420 carried by the support member 410. The therapy electrodes 420 can be individual electrodes that are arranged in a grid array having M columns and N rows. The electrode array 400 can have several other arrangements of electrodes 420, such as concentric circles, elongated lines, or many other patterns. Each of the electrodes 420 can be independently coupled to a pulse system so that individual electrodes 420 can be activated or inactivated using the controller 130 (FIG. 1) and the pulse system 140 (FIG. 1). The electrode array 400 is typically implanted into the patient so that the electrodes 420 are placed generally over or proximate to a target location T for stimulation. In many embodiments, the target location T can be at the surface of the cortex, along the spinal cord, or within a deep brain region of a patient depending upon the particular treatment being applied to the patient.

Figure 4A:
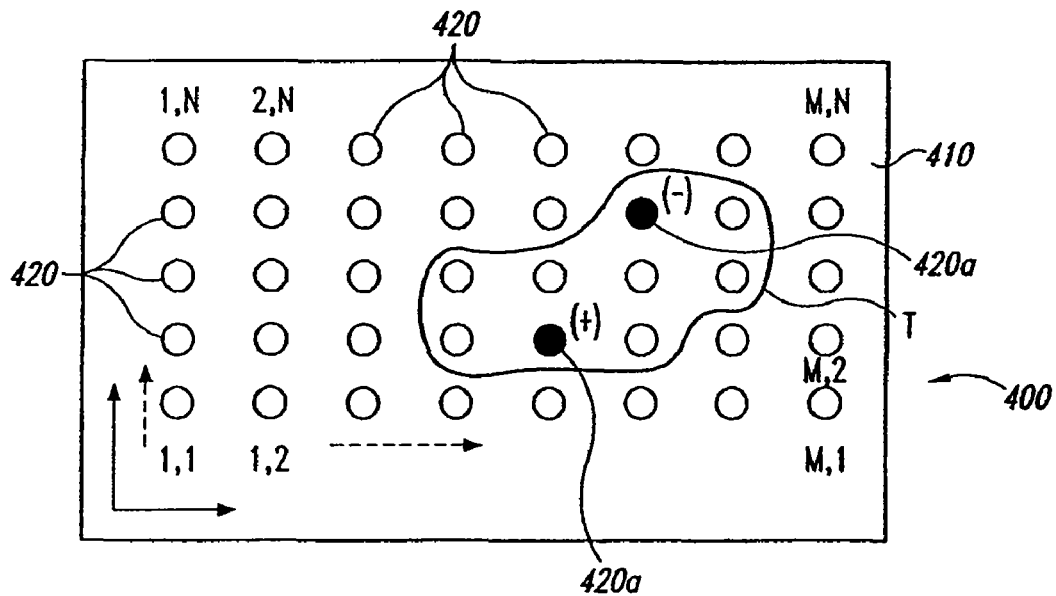
FIGS. 4A-L illustrate various examples of using the system of FIG. 1 to optimize the configuration of the electrodes in accordance with an embodiment of the methods of FIGS. 2 and 3.
Figure 4B:
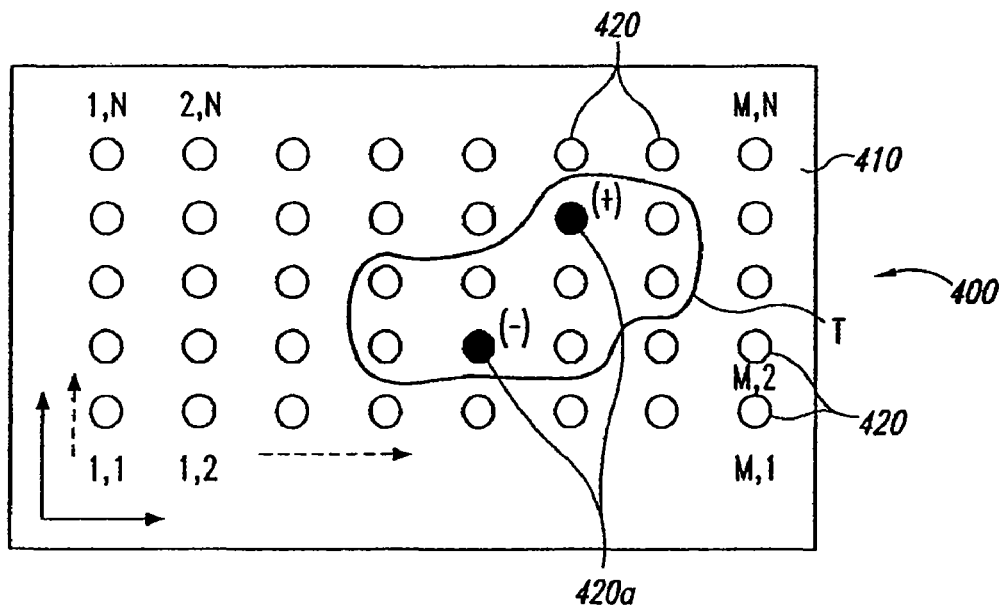
Figure 4C:
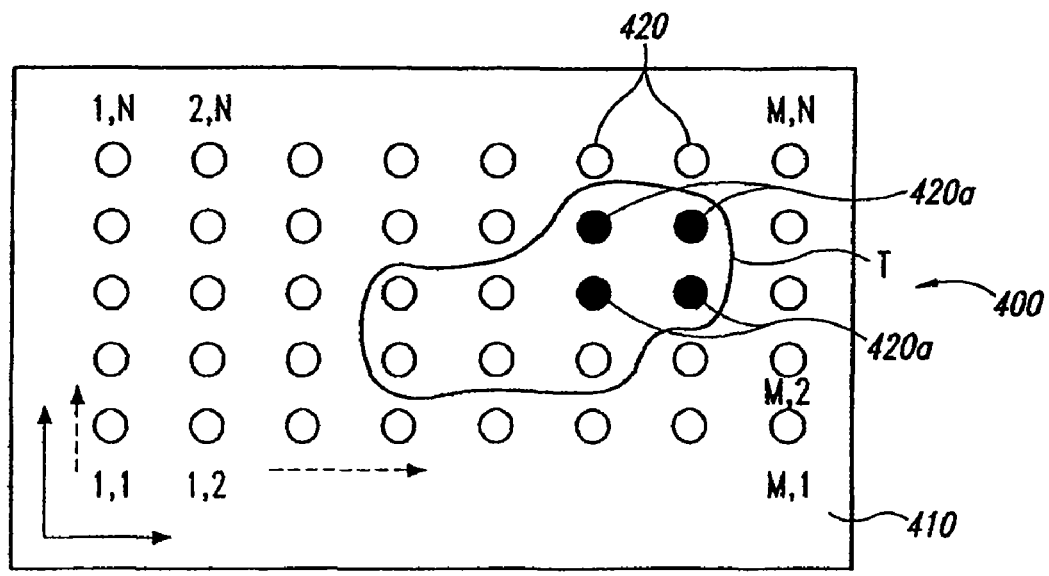
Figure 4D:
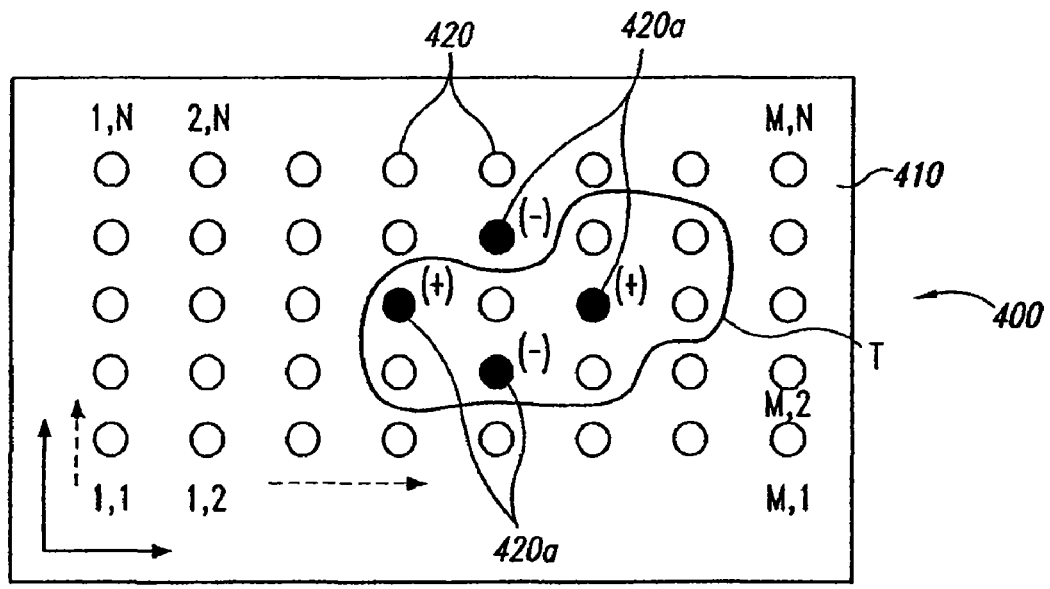
Figure 4E:
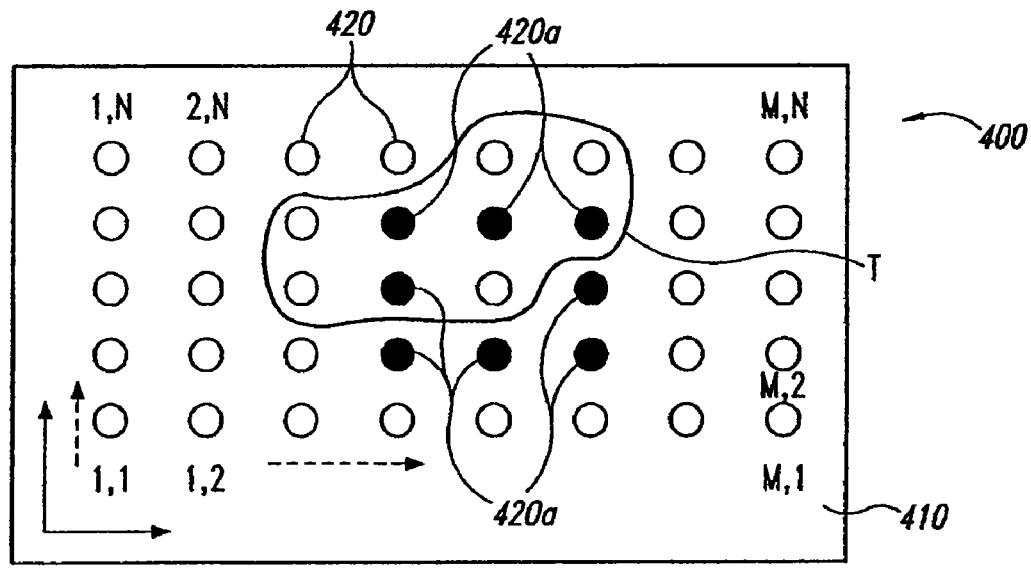

FIGS. 4A and 4B illustrate two alternate embodiments of selecting therapy electrode configurations. Referring to FIG. 4A, a setup configuration of two active electrodes 420a can be selected such that the electrodes are within the target location T. One of the active electrodes 420a can be biased with a positive polarity and the other active electrode 420a can be biased with a negative polarity. Referring to FIG. 4B, a subsequent iteration of the process can include selecting an alternate configuration of therapy electrodes in which the polarity of the active electrodes 420a is switched. FIGS. 4C-4E illustrate alternate embodiments of selecting different configurations of therapy electrodes using the analyzing procedure 360 explained above with reference to FIG. 3. As can be seen from FIGS. 4C-4E, the active therapy electrodes 420a can be inside and/or outside of the target location T. FIG. 4C illustrates an embodiment in which all of the active electrodes 420a are within the target location and adjacent to one another, and FIGS. 4D and 4E illustrate embodiments in which at least some of the active electrodes 420a are outside of the target location T and one or more inactive electrodes 420 are between some of the active electrodes 420a. It will be appreciated that the analyzing procedure 360 can select any configuration of therapy electrodes 420 in the M×N electrode array 400 such that any combination of electrodes 420 can be active electrodes.

Figure 4F:
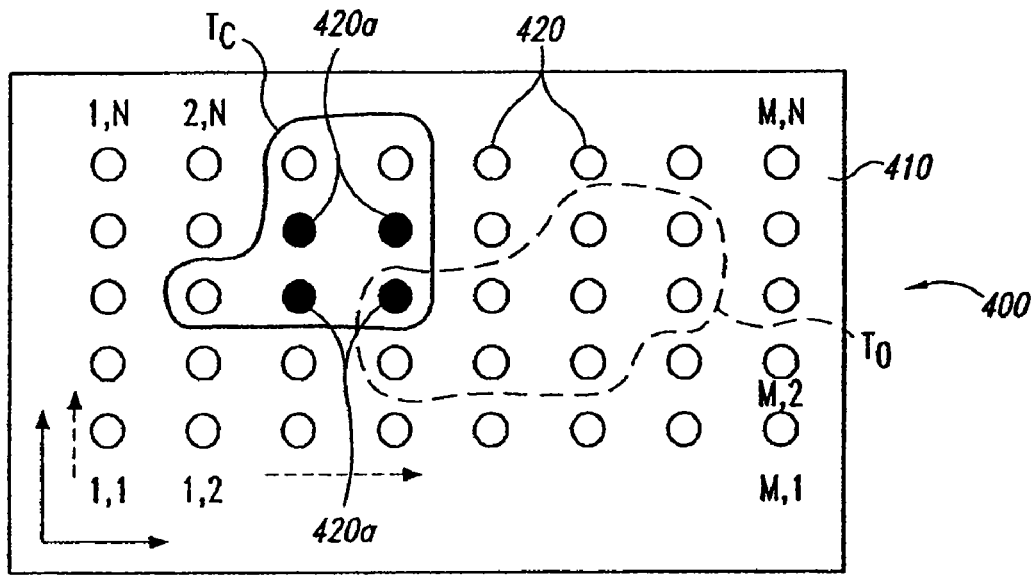

FIG. 4F illustrates another aspect of selecting a desired configuration of therapy electrodes in which an original target location $T_o$ (shown in broken lines) has changed to a current target location $T_c$. The shift from the original target location $T_o$ the current target location $T_c$ can be caused by several generally unpredictable factors. The methods 200 and 300 can compensate for such a target location shift without additional surgery because the therapy electrodes can be optimized using an external control and indirect coupling with the pulse system and/or or the electrode array. Thus, the application of the stimulus can be changed as the target location of neural activity shifts to provide efficacious treatment over a long period of time.

Figure 4G:
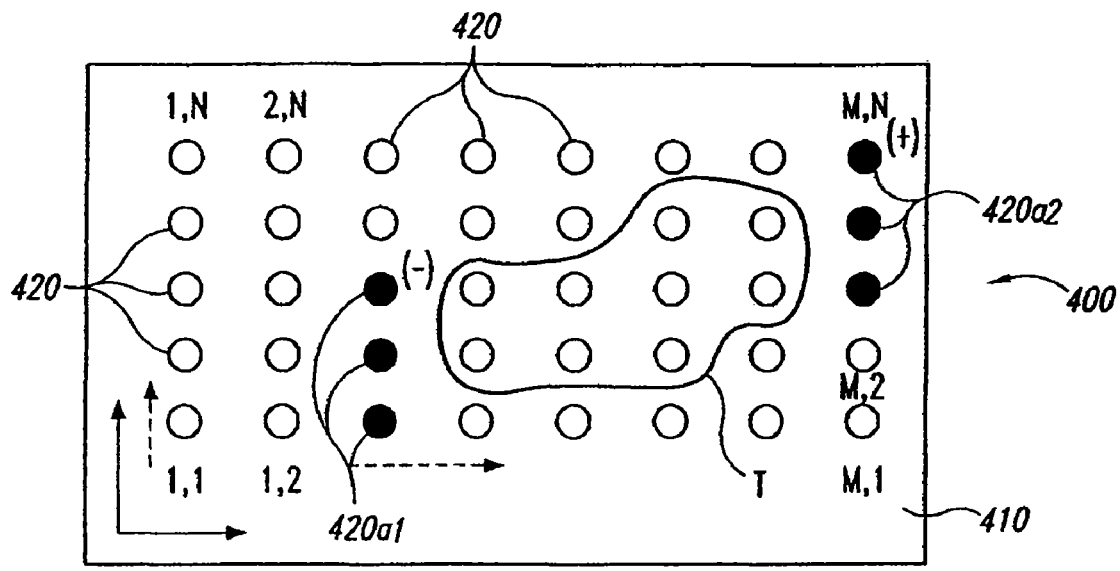
Figure 4H:
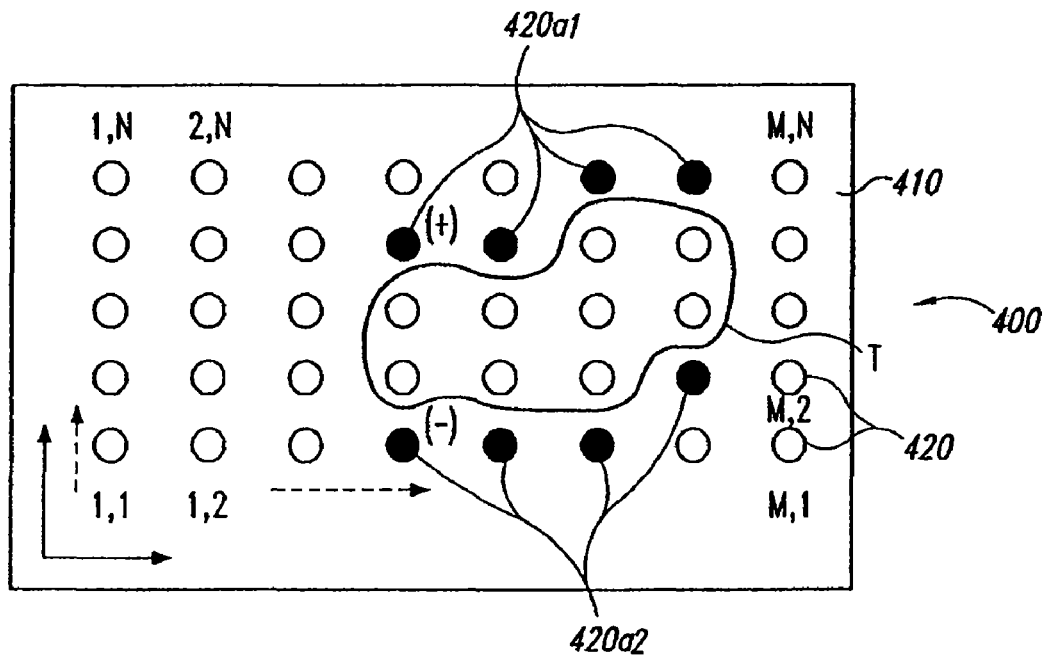

FIGS. 4G and 4H illustrate different embodiments of therapy electrical configurations that can be selected in the analyzing procedure 360 in which several electrodes on opposite areas of the target location are activated with a common polarity. Referring to FIG. 4G, for example, this embodiment illustrates a series of active electrodes on opposite ends of the target location T. One embodiment of this configuration applies a common polarity to a first set $420_{a1}$ of active electrodes and an opposite polarity to a second set $420_{a2}$ of active electrodes. Another embodiment can apply the same polarity to all of the active electrodes in both of the sets $420_{a1}$ and $420_{a2}$. FIG. 4H illustrates a related embodiment in which a number of electrodes on opposite sides of the target location T are active electrodes. The electrode configuration shown in FIG. 4H can also apply a common polarity to all of the active electrodes on each side of the target location T or all of the electrodes on both sides of the target location T.

Figure 4I:
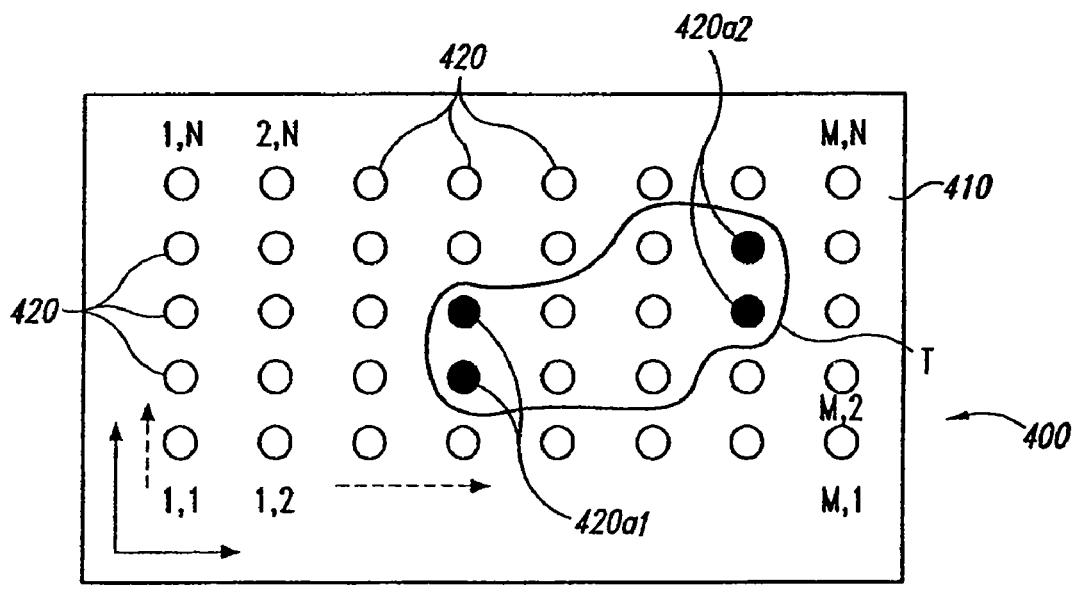
Figure 4J:
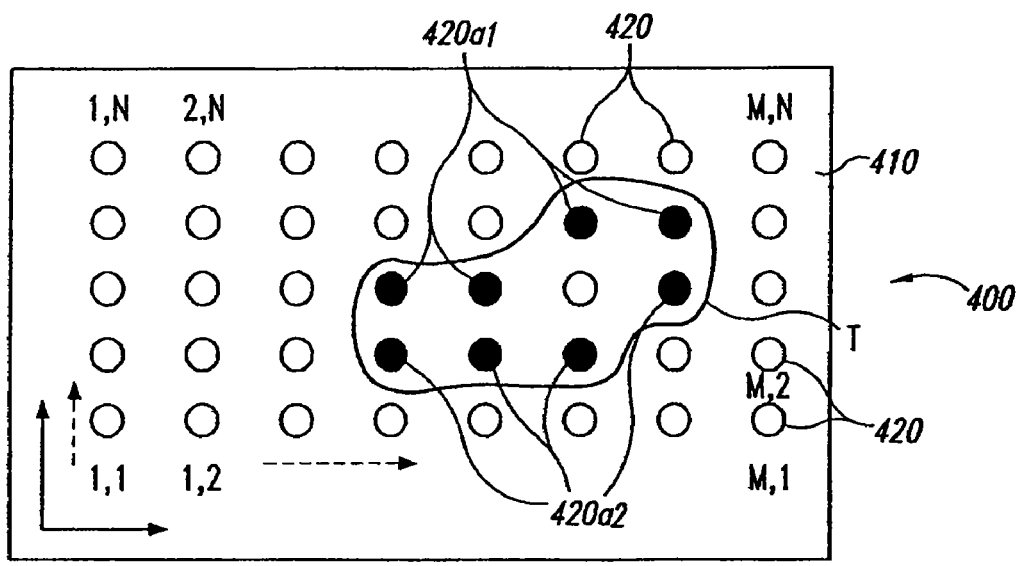

FIGS. 4I and 4J illustrate additional embodiments of electrode configurations that can be selected in the analyzing procedure 360 and then tested in the stimulation procedure 320. FIG. 4I illustrates an embodiment in which a first set $420_{a1}$ of active electrodes has a common polarity at one end of the target location T, and a second set $420_{a2}$ of active electrodes is located at an opposite end of the target location T. The polarity of the electrodes in the second set $420_{a2}$ can be opposite or the same as those of the active electrodes in the first subset $420_{a1}$. FIG. 4J illustrates a similar embodiment in which a first set $420_{a1}$ of active electrodes is located within the target location T along one side, and a second set $420_{a2}$ of active electrodes is located within a target location T along an opposite side. The electrodes in the first set $420_{a1}$ can have one polarity, and the electrodes in the second set $420_{a2}$ can have an opposite polarity.

Figure 4K:
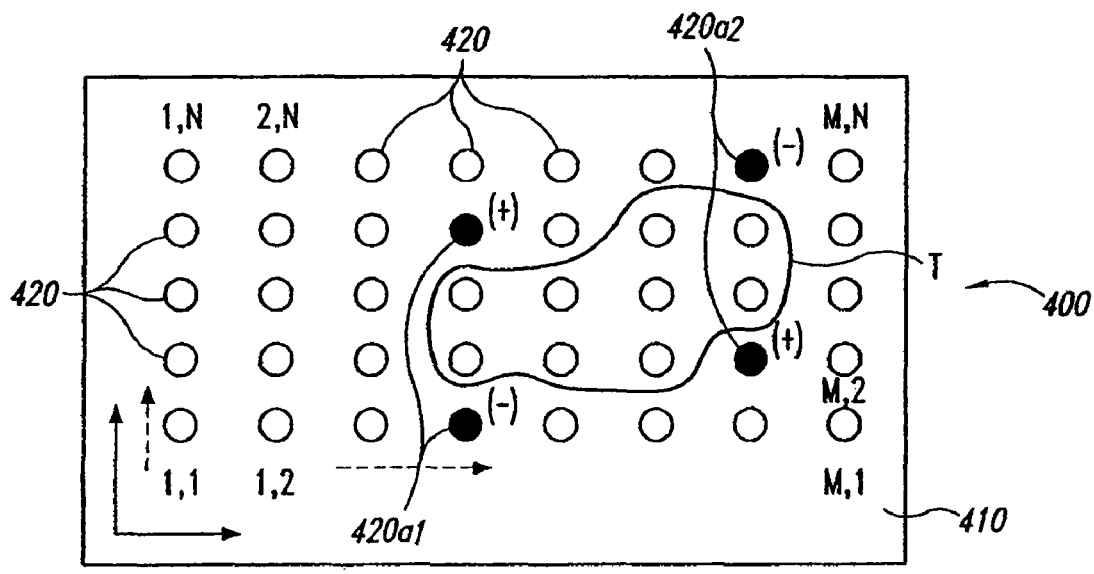
Figure 4L:
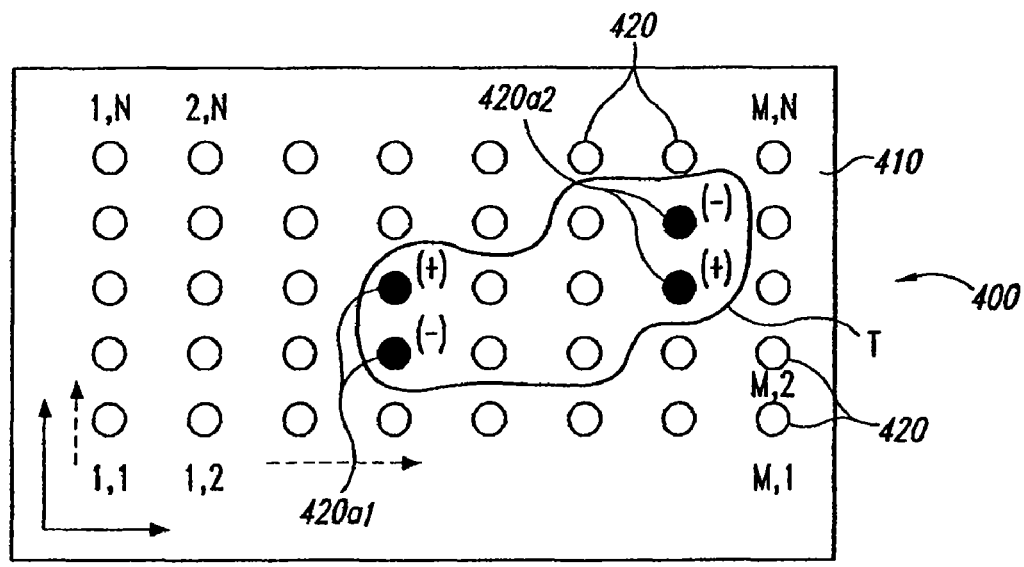

FIGS. 4K and 4L illustrate additional embodiments of therapy electrode configurations that can be selected in the analyzing procedure 360 and then tested in the stimulation procedure 320. Referring to FIG. 4K, this embodiment illustrates a first set $420_{a1}$ of active electrodes at one end of the target location T and a second set $420_{a2}$ of active electrodes at an opposite end of the target location T. The active electrodes in the first set $420_{a1}$ can have opposite polarities and similarly the active electrodes in the second set $420_{a2}$ can have opposite polarities. The active electrodes in the first and second sets $420_{a1}$ and $420_{a2}$ can be located outside of the target location T as shown in FIG. 4K. FIG. 4L illustrates a related embodiment in which the active electrodes in the first set $420_{a1}$ have opposite polarities, and the active electrodes in the second set $420_{a2}$ have opposite polarities. The active electrodes in the first and second sets $420_{a1}$ and $420_{a2}$ shown in FIG. 4L are located within the boundaries of the target location T. It will be appreciated that the invention can have several additional embodiments in which the individual sets of electrodes can be inside, outside, inside and outside, and have different combinations of polarities.

Figure 5:
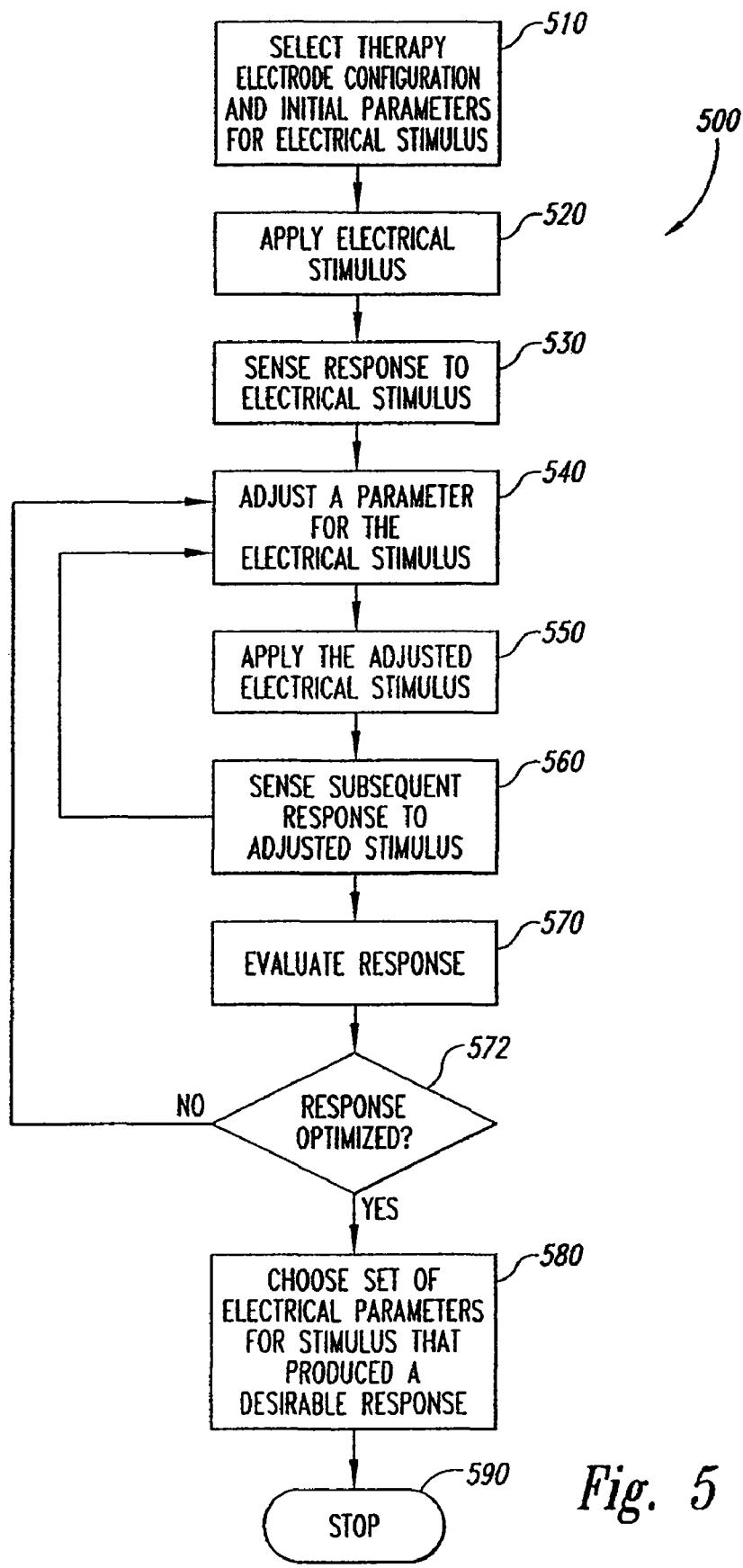
FIG. 5 is a flow diagram of a method for optimizing the stimulus parameters that can be used in the method of FIG. 2 in accordance with an embodiment of the invention.

Another aspect of the invention is optimizing the parameters for the electrical stimulus in addition to or in lieu of optimizing the configuration of therapy electrodes. FIG. 5 is a flow diagram of a method for optimizing the desired parameters for the electrical stimulus in accordance with an embodiment of the invention. In this embodiment, the method 500 can include a setup procedure 510 in which a therapy electrode configuration and the initial parameters for the electrical stimulus are selected. The configuration of therapy electrodes can be the optimized configuration from the method 300 explained above with reference to FIG. 3, or it can be another configuration input by a practitioner or retrieved from memory in the controller. The same configuration of therapy electrodes is generally maintained throughout the method 500. After performing the setup procedure 510, the method 500 continues with a first stimulating procedure 520 in which the electrical stimulus is applied to the selected configuration of therapy electrodes using the initial parameters of the electrical stimulus. A response in the patient to the initial electrical stimulus is sensed in a first sensing procedure 530. The procedures 510-530 accordingly provide a response to an initial electrical stimulus based upon the initial stimulus parameters to provide a baseline response.

The method 500 continues with an adjusting procedure 540 in which one of the stimulus parameters for the electrical stimulus is adjusted, and then a second stimulating procedure 550 in which the adjusted stimulus is applied to the therapy electrodes. A response to the adjusted stimulus is then determined using a second sensing procedure 560. The method 500 can repeat the procedures 540-560 several times for each of the parameters of the electrical stimulus to develop a plurality of responses for each parameter.

The method 500 can then continue with an evaluation procedure 570 in which the responses are evaluated to determine specific values for the stimulus parameters that provide an efficacious result. The evaluation procedure 570 can include a determination routine 572 that determines whether a parameter of the stimulus has been optimized. If the response for a parameter is not optimized, then the method can continue by repeating the procedures 540-560 for the parameters that are not within a desired range. However, if the response is optimized, then the determination routine 572 can continue to a final selection procedure 580 in which a set of electrical parameters that produce a desirable response are selected.

Figure 6:
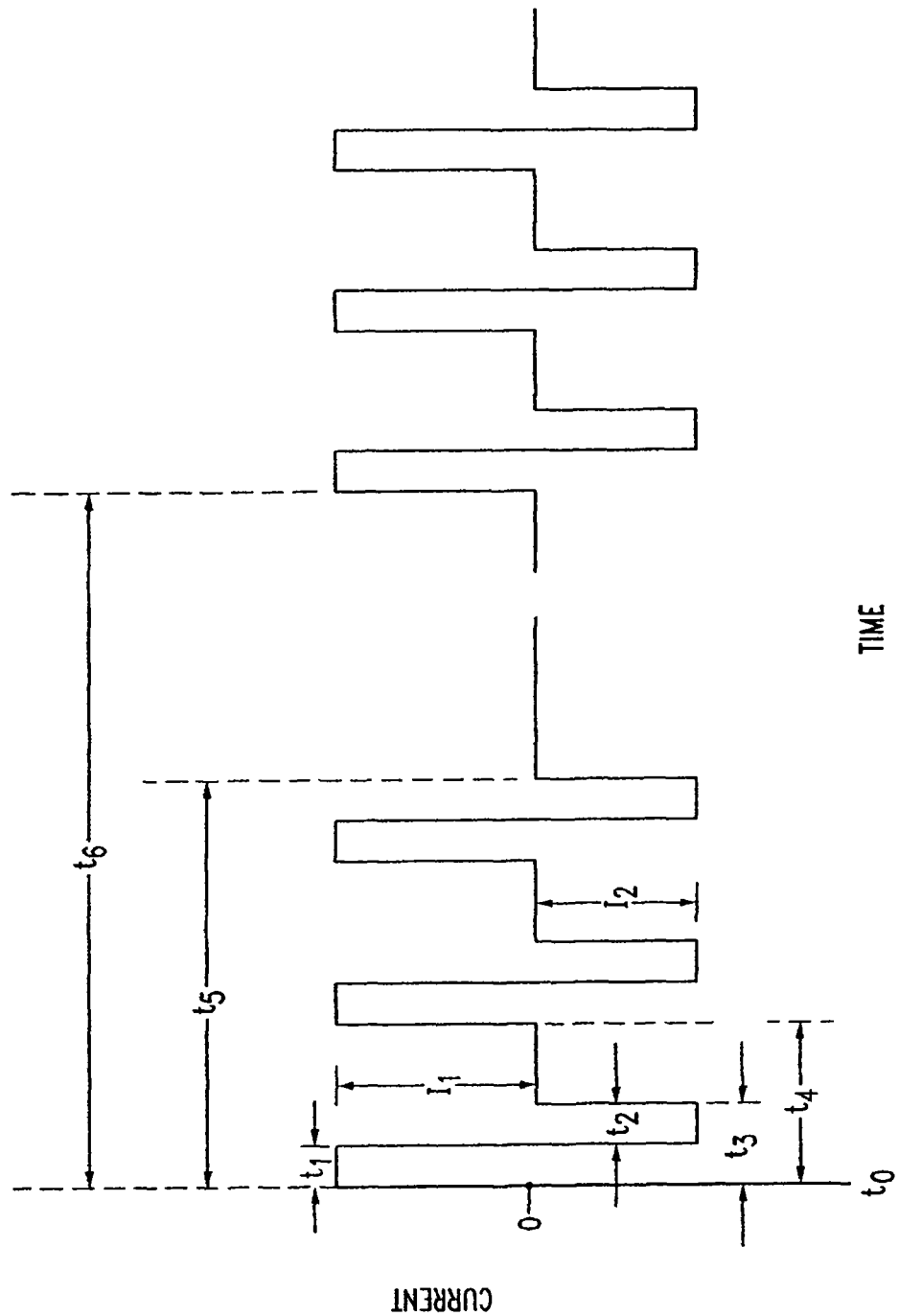
FIG. 6 is a diagram illustrating an example of several stimulus parameters that can be optimized using an embodiment of the method of FIG. 5.

FIG. 6 is a graph illustrating some of the stimulus parameters that can be optimized using the method 500. A stimulus start time $t_o$ defines the initial point at which an electrical or magnetic pulse is applied to the therapy electrodes. For a biphasic waveform, the parameters typically include a pulse width $t_1$ for a first phase, a pulse width $t_2$ for a second phase, and a stimulus pulse width $t_3$ for a single biphasic pulse. The pulse can alternatively be a monophasic pulse. The parameters can also include a stimulus repetition rate $1/t_4$ corresponding to the frequency of the pulses, a stimulus pulse duty cycle equal to $t_3$ divided by $t_4$, a stimulus burst time $t_5$ that defines the number of pulses in a pulse train, and/or a stimulus pulse repetition rate $1/t_6$ that defines the stimulus burst frequency. Another parameter of the electrical stimulus is the intensity of the current $I_1$ for the first phase and the current intensity $I_2$ for the second phase of each pulse. In another embodiment, a continuous pulse train can be used such that $t_5=t_6$.

In a typical application, one of the parameters is adjusted for each application of the stimulus while maintaining the other parameters constant to determine the affect that adjusting the one parameter has on the response in the patient. Each of the parameters are believed to be independent from one another, thus one of the parameters can be optimized by applying a number of different stimuli using different values for the parameter to determine whether increasing or decreasing the parameter enhances the efficacy of the stimulus. Once it is determined whether increasing or decreasing the parameter provides a better result, then the parameter can be further increased or decreased (whichever is more desirable) until the effectiveness of the stimulation degrades. The optimized value for a particular stimulus parameter can then be stored in memory, and then a different stimulus parameter can be optimized using a similar procedure for that parameter. As such, one or more of the stimulus parameters can be optimized using this procedure.

The embodiments of the methods 200, 300 and 500 described above can be used to optimize procedures for cortical stimulation, spinal stimulation, deep brain stimulation, and peripheral stimulation for a number of different applications. The spinal stimulation and certain aspects of the cortical stimulation can be used to mask pain, such as back pain, phantom limb pain experienced by amputees, or pain in the lower extremities. The deep brain stimulation can be optimized to treat movement disorders (e.g., Parkinson's disease, distonia, etc.), depression, or other functions related to deep brain neural activity. The methods can also be used to optimize therapies for cortical stimulation that enhance learning functions, restore motor functions (e.g., use of muscle groups affected by stroke or other trauma), and treating diseases or seizures (e.g., Alzheimer's, epilepsy, etc.). Many of the embodiments of the methods 200, 300 and 500 for masking pain involve applying supra-threshold activation stimuli to the therapy electrodes. On the other hand, several of the cortical neural-stimulation procedures that are not directed toward masking pain but rather seek to enhance existing functions (e.g., learning) or rehabilitate impaired functions (e.g., brain damage) use sub-threshold activation stimuli that do not exceed the membrane activation threshold of a population of neurons in the target stimulation site. Several embodiments of the methods 200, 300 and 500 that are directed more specifically toward sub-threshold optimization of the neural-stimulation procedures are described below with reference to FIG. 7.

C. Sub-Threshold Optimization Methods

Figure 7:
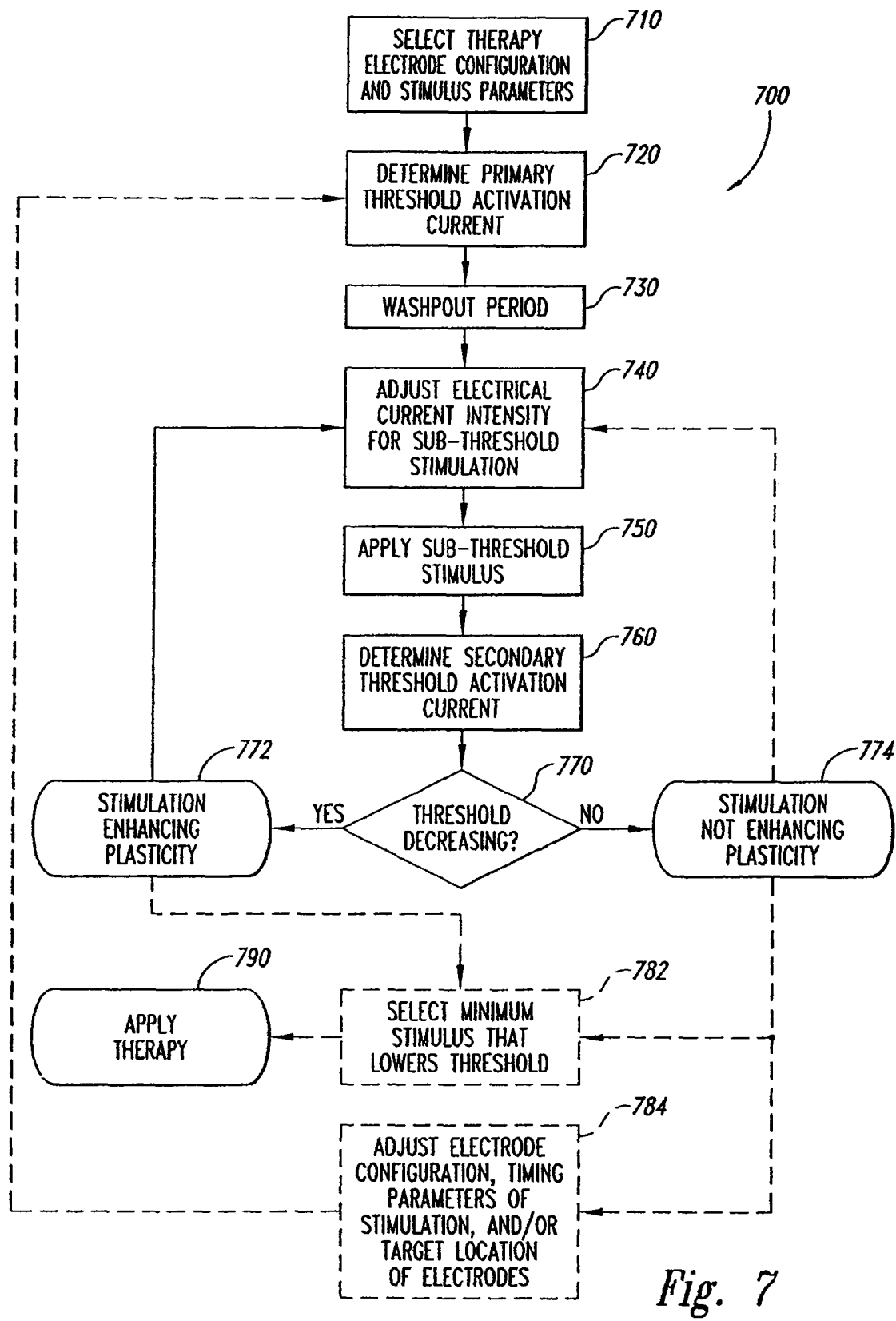
FIG. 7 is a flow diagram of a method for optimizing the electrode configuration and/or stimulus parameters for inducing and/or enhancing neural-plasticity using sub-threshold stimulation in accordance with an embodiment of the invention.

FIG. 7 is a flow diagram illustrating an embodiment for optimizing a sub-threshold simulation therapy. Sub-threshold simulation involves training and/or recruiting neurons to perform a neural-function. The target location can be a site where neural-plasticity is occurring or is expected to occur. The present inventors believe that neurons become more likely to be able to carry out desired neural-functions for enhancing, repairing or restoring functionality after being stimulated electrically at a level below the membrane activation threshold for a significant population of neurons at the target site. The present inventors also believe that certain sub-threshold simulation lowers the threshold at which neurons are activated in response to physical or cognitive input to produce a lasting change in the membrane potential such that the neurons may eventually "fire" in response to motor or cognitive functions after termination of the stimulus. The optimization procedure for sub-threshold simulation accordingly seeks to select stimulus parameters that produce the desired neural-activity at the lowest level of stimulation.

Referring to the flow diagram of FIG. 7, this figure illustrates an embodiment of a method 700 including a setup procedure 710 in which the configuration of therapy electrodes and the parameters for the stimulus are selected. The therapy electrode configuration and the stimulus parameters can be determined by optimizing them as described above with reference to FIGS. 1-6. The method 700 then continues with an activation threshold determination procedure 720 that determines the intensity of the electrical current for the stimulus that causes a reaction in a population of the neurons at the target location to exceed the membrane activation threshold. In one embodiment, the threshold determination procedure 720 involves sensing responses in the patient that are related to changes in the membrane potential of the neurons. It is difficult to measure the actual membrane potential of a neuron, so the determination procedure 720 generally measures a tangible response that is a surrogate for the change in the membrane potential. One such surrogate measurement of changes in the membrane potential is the EMG response to the stimulus applied to the therapy electrodes. The threshold determination procedure 720 accordingly involves adjusting the stimulus parameters until the electrical current intensity just begins to produce an EMG response indicating that a significant population of neurons at the target location have just exceeded their membrane potential. After the EMG indicates a threshold electrical current, the method 700 includes a delaying period 730 in which the effects of the supra-threshold stimulus are allowed to "wash out" from the neurons.

The method 700 further includes a sub-threshold stimulation procedure involving a selecting procedure 740 in which the intensity of the electrical current is lowered to a "sub-threshold" level, and a stimulation procedure 750 in which the sub-threshold stimulus is applied to the configuration of therapy electrodes. The selecting procedure 740 can involve selecting an electrical current that is a percentage of the threshold electrical current identified in the threshold determination procedure 720. In one embodiment, the sub-threshold current intensity is initially selected to be from approximately 40%-99% of the threshold electrical current membrane. After the sub-threshold electrical current intensity has been applied to the electrode configuration in the stimulation procedure 750, a sensing procedure 760 determines whether the sub-threshold stimulus reduced the membrane activation threshold for a population of neurons.

The sensing procedure 760 can proceed in a manner similar to the activation threshold procedure 720 explained above by applying an electrical pulse having a sensing current intensity above the sub-threshold stimulus applied in the stimulating procedure 740 and below the initial threshold stimulus level that was measured in the threshold determining procedure 720. For example, if the threshold current for the threshold stimulus that produced the threshold activation was 10 mA and the sub-threshold current applied in the stimulating procedure 750 was 7 mA, then the sensing procedure 760 can start with a sensing current intensity of 7.5 mA and incrementally increase the sensing current intensity (e.g., by 0.5 mA increments). The sensing current is increased until the EMG measurements indicate that the membrane potential of a population of neurons has been exceeded. This is a ramp up procedure that works up from the sub-threshold current intensity applied in the stimulating procedure 750. An alternate embodiment is a ramp down procedure in which the sensing current intensity is initially set at a level near the threshold current intensity (e.g., 90-99%) and works down until a threshold activation is not detected. In either case, the sensing procedure 760 determines a secondary threshold current intensity corresponding to a change in the membrane threshold activation.

The method 700 then continues with an analyzing procedure 770 that determines whether the secondary current intensity is less than the initial threshold current intensity. If so, then the method 700 continues to identify that the stimulation is enhancing the plasticity of the neurons at stage 772, and then the method 700 either repeats procedures 740-760 with a lower sub-threshold electrical current intensity or it selects an optimized sub-threshold current intensity for use with the patient at stage 782. If the analyzing procedure 770 determines that the threshold activation of the neurons is not decreasing, then the method 700 proceeds to stage 774. In one embodiment in which a number of different electrical current intensities have reduced the activation threshold of the neurons, the method 700 continues from stage 774 to stage 782 to select the most effective sub-threshold current intensity that has been tested for use on the patient. In another embodiment in which the stimulus parameters applied to the therapy electrodes have not decreased the activation threshold, the method 700 can repeat procedures 740-770 to determine whether a different electrical current intensity can produce a lower activation threshold. In still another embodiment in which the activation threshold does not decrease after application of the stimulus, the method 700 can continue with stage 784 that involves adjusting the electrical configuration, the timing parameters of the electrical stimulation, and/or the target location of the electrodes. After stage 784, the method 700 can then proceed with repeating procedures 740-770 to determine whether the activation threshold can be lowered by applying the new stimulus parameters to the therapy electrodes in accordance with the changes that were made in stage 784.

From the foregoing, it will be appreciated that specific embodiments of the invention have been described herein for purposes of illustration, but that various modifications may be made without deviating from the spirit and scope of the invention. For example, the electrode arrays and sensing devices could be configured for use in cardiac applications to optimize implantable pacemakers or implantable defibrillators. It will be appreciated that the applications of the invention in the field of cardiology are embodiments of optimizing a peripheral stimulation treatment. Many aspects of the invention are also applicable to magnetic stimulation in addition to or in lieu of electrical stimulation. In magnetic applications, the parameters for the stimulation can be automatically set using the algorithms explained above for electrical stimulation; but, instead of selecting different configurations of a subcutaneous array of electrodes, the location and configuration of a magnetic transducer can be moved externally relative to the body. In still further applications of the inventions, many of the embodiments of the apparatus and methods can be particularly useful for optimizing spinal cord stimulation therapies and procedures. Accordingly, the invention is not limited except as by the appended claims.

What is claimed is:

1. A method for treating a patient, comprising:
   addressing at least one of patient pain and depression by applying an electrical stimulus having a plurality of stimulus parameters to a selected configuration of therapy electrodes that have been installed at a target therapy site of the central nervous system of the patient, wherein applying the electrical stimulus includes applying the electrical stimulus at a sub-threshold current intensity level relative to a threshold level for neurons at the target therapy site;
   identifying a change in a sensed parameter via MR spectroscopy;
   selecting an alternate configuration of therapy electrodes and/or an alternate electrical stimulus based at least in part on the change in the sensed parameter identified via MR spectroscopy, wherein the alternate electrical stimulus includes decreasing the sub-threshold current intensity to a lower level;
   applying a further electrical stimulus to the patient in accordance with the alternate configuration of therapy electrodes and/or an alternate electrical stimulus, and
   determining whether the application of the alternate electrical stimulus further decreased the membrane activation threshold for the population of neurons.

2. The method of claim 1 wherein identifying a change in a sensed parameter includes identifying a change in a sensed parameter that corresponds to a shift in the target therapy site.

3. The method of claim 1, further comprising repeating (a) decreasing the sub-threshold current intensity to a lower level, (b) re-applying the decreased sub-threshold stimulus with the lower current intensity to the neurons, and (c) further determining whether the application of the decreased sub-threshold current intensity further decreased the membrane activation threshold for the population of neurons until the membrane activation threshold by or to a selected level.

4. The method of claim 1 wherein applying a sub-threshold electrical stimulus includes applying the electrical stimulus from a location within the patients skull, external to a cortical surface of the patient's brain.

5. The method of claim 1 wherein applying an electrical stimulus includes applying an electrical stimulus at a sub-cortical location.

6. The method of claim 1 wherein applying an electrical stimulus includes applying an electrical stimulus to a deep brain location.

* * * * *